(12) United States Patent
Alhadrami et al.

(10) Patent No.: US 11,564,964 B2
(45) Date of Patent: Jan. 31, 2023

(54) COMPOSITIONS AND METHODS FOR THE TREATMENT OF CORONAVIRUS INFECTION

(71) Applicant: King Abdulaziz University, Jeddah (SA)

(72) Inventors: Hani A. Alhadrami, Jeddah (SA); Ahmed M. Sayed, Beni-Suef (EG); Hossam M. Hassan, Beni-Suef (EG); Usama R. Abdelmohsen, Minia (EG); Mostafa E. Rateb, Paisley (GB)

(73) Assignee: King Abdulaziz University, Jeddah (SA)

( * ) Notice: Subject to any disclaimer, the term of this patent is extended or adjusted under 35 U.S.C. 154(b) by 48 days.

(21) Appl. No.: 17/179,447

(22) Filed: Feb. 19, 2021

(65) Prior Publication Data
US 2022/0265746 A1    Aug. 25, 2022

(51) Int. Cl.
  *A61K 36/28* (2006.01)
  *A61K 31/343* (2006.01)

(52) U.S. Cl.
  CPC ............ *A61K 36/28* (2013.01); *A61K 31/343* (2013.01)

(58) Field of Classification Search
  None
  See application file for complete search history.

(56) References Cited

PUBLICATIONS

Scheinder et al., A Contribution to Analytics and Pharmacology of Cnicin, 1987, Planta medica, pp. 247-250.*
2021 https://www.rockstepsolutions.com/blog/difference-between-in-vivo-and-in-vitro-testing/.*
Sanders et al., Pharmacologic Treatments for Coronavirus Disease 2019 (COVID-19) A Review, 2020, JAMA, 323: 1824-1836.*
2020 https://www.fda.gov/media/144118/download Emergency Use Authorization for bamlanivimab 500 mg IV: Canter for Drug Evaluation and Research Review.*
Erel et al., 2011, Secondary metabolites of Centaureacalolepis and evaluation of cnicin for anti-inflammatory, antioxidant, and cytotoxic activities, Pharmaceutical Biology, 49:8, 840-849.*
Paraiso et al., Potential use of polyphenols in the battle against COVID-19, 2020, Current Opinion in Food Science, 32: 149-155.*
Paun et al., Chemical and Bioactivity Evaluation of Eryngium planum and Cnicus benedictus Polyphenolic-Rich Extracts, 2019, BioMed Research International, vol. 2019, pp. 1-10.*
Hwang et al., "Synthesis and anti-viral activity of a series of sesquiterpene lactones and analogues in the subgenomic HCV replicon system", Bioorganic & Medicinal Chemistry 14 (2006) 83-91.
Szabo et al., "The Antimicrobial Activity of the *Cnicus benedictus* L. Extracts", Tom. XVI / 1, 2009, pp. 126-128.
Ulbricht et al., "An Evidence-Based Systematic Review of Blessed Thistle (*Cnicus benedictus*) by the Natural Standard Research Collaboration", Journal of Dietary Supplements, vol. 5(4), 2008.

\* cited by examiner

*Primary Examiner* — Terry A McKelvey
*Assistant Examiner* — Catheryne Chen
(74) *Attorney, Agent, or Firm* — WCF IP

(57) ABSTRACT

Methods for treating coronavirus infection, such as an infection caused by SARS-Cov-2 or MERS-Cov, in a subject in need thereof include administering to the subject a therapeutically effective amount of a composition comprising cnicin. Compositions comprising cnicin include an extract of *C. benedictus* or purified cnicin.

3 Claims, 9 Drawing Sheets

Specification includes a Sequence Listing.

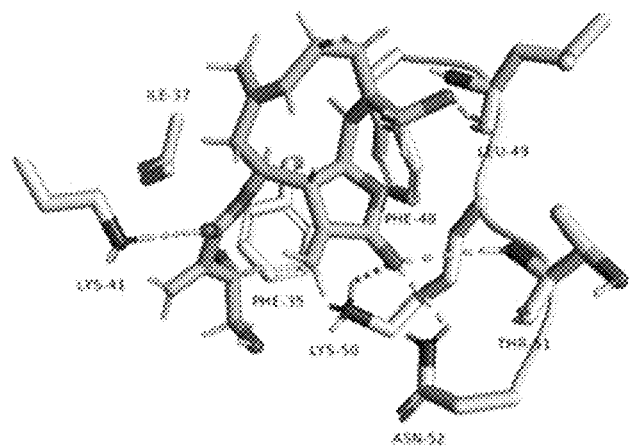
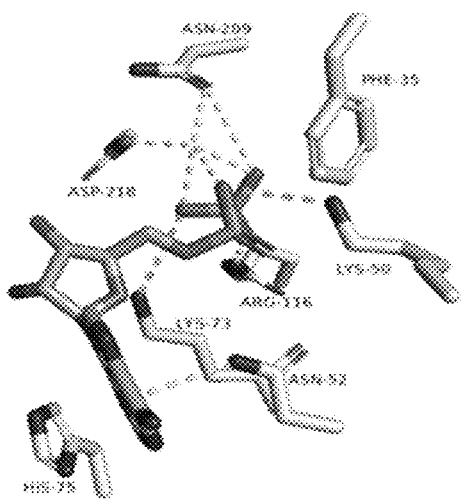
FIG. 6A                FIG. 6B
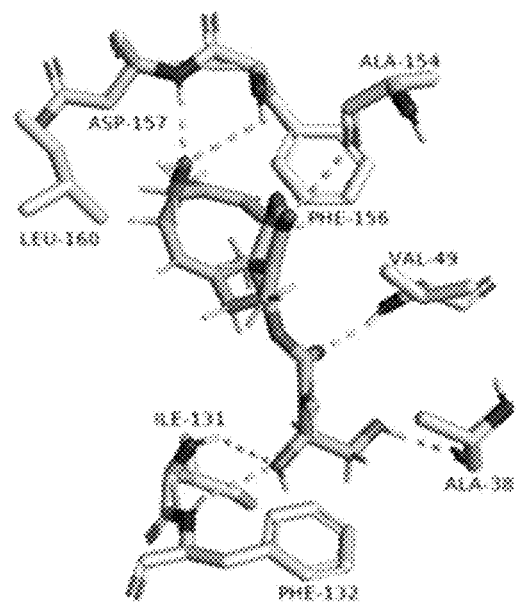
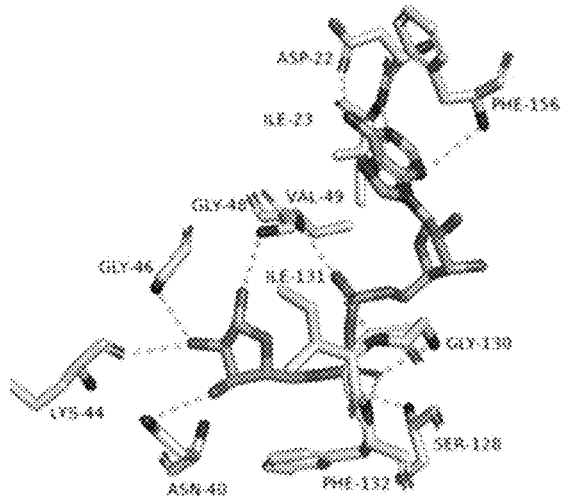
FIG. 6C                FIG. 6D

COMPOSITIONS AND METHODS FOR THE TREATMENT OF CORONAVIRUS INFECTION

FIELD OF THE INVENTION

The invention is generally related to the use of cnicin for treating a coronavirus infection, such as an infection caused by SARS-Cov-2 or MERS-Cov.

BACKGROUND OF THE INVENTION

Severe acute respiratory syndrome coronavirus-2 (SARS-CoV-2) has created an unprecedented global health crisis[1]. It is a zoonotic virus with highly contagious properties as compared to the Middle East Respiratory Syndrome virus (MERS-CoV)[2]. SARS-CoV-2 is from the Coronaviridae family and causes an acute respiratory disease which could be lethal, with about a 10.2% mortality rate. The disease can cause death due to severe alveolar destruction and hemorrhage as well as progressive respiratory failure[3]. Coronaviruses are further divided into two subfamilies; coronavirinae and torovirinae. The coronavirinae subfamily is further categorized into four genera: $\alpha$-, $\beta$-, $\gamma$-, and $\delta$-coronaviruses according to the classification of the Worldwide Committee for Logical Classification of Infections[4]. SARS-CoV-2 is a positive-sense, single-stranded RNA $\beta$-coronavirus that infects mammals and is assumed to come from bats[5]. Additionally, it has one of the biggest genomes among other RNA viruses[6,3]. This genome is wrapped with a nucleocapsid protein (N) inside an envelope consisting of three other structural proteins, i.e. the membrane protein (M), the envelope protein (E), and the spike protein (S). The S protein gives coronaviruses an outer crown appearance; therefore, the virus is named "corona" in Latin which means "the crown"[3]. It is also the key protein that mediates the virus entry into the host cell via binding to the host angiotensin-converting enzyme 2 (ACE2) receptors[7,8].

The SARS-CoV-2 pandemic is a pressing challenge to discover practical approaches and pathways for managing and treating the virus[9]. Moreover, scientists are searching for possible drug targets to develop effective therapeutics to control this pandemic. Recent findings have given the scientific community a lot of information about SARS-CoV-2 structural proteins and those involved in the viral nucleic acid replication and other host-specific proteins that have a vital role in the pathogenesis of the virus[9,10].

Natural products are considered a precious trove of drug leads[11]. Various natural products (e.g. baicalin, ivermectin, artemisinin) were recently reported as promising SARS-CoV-2 inhibitors. They target multiple viral and host-specific proteins involved in the viral processing (viral protease), viral entry into host cells, viral replication, and its release from the infected cells[12]. Moreover, enormous in silico studies have also been conducted at the beginning of the crisis, suggesting a wide range of natural products from several chemical classes to be promising anti-SARS-CoV-2 agents[12,13]. However, new antiviral agents targeting coronaviruses are still needed.

SUMMARY

It has been discovered that *C. benedictus* extract (CBE) inhibits corinovirus replication and thus represents a new antiviral agent for the treatment of coronavirus infection.

An aspect of the disclosure provides a method of treating a coronavirus infection in a subject in need thereof, comprising administering to the subject a therapeutically effective amount of a composition comprising cnicin. In some embodiments, the composition is an extract of *C. benedictus*. In some embodiments, the composition comprises purified cnicin. In some embodiments, the coronavirus is SARS-CoV-2. In some embodiments, the coronavirus is MERS-CoV.

BRIEF DESCRIPTION OF THE DRAWINGS

FIGS. 6A-F. Binding modes of cnicin inside the binding sites of SARS CoV-2 nsp12, nsp3, nsp15 (A, C, and E, respectively) during 100 ns MDS along with the binding modes of the corresponding co-crystallized ligands (B, D, and F, respectively).

DETAILED DESCRIPTION

Embodiments of the disclosure provide an extract of *C. benedictus* that inhibits coronavirus replication.

*Cnicus benedictus* (blessed thistle) is a thistle-like plant in the family Asteraceae, native to the Mediterranean region, from Portugal north to southern France and east to Iran. It is known in other parts of the world, including parts of North America, as an introduced species and often a noxious weed.

To obtain an extract, plants and/or plant parts (e.g., flowers, leaves and/or stems) can be isolated and ground (e.g., coarsely grinded using an electrical blender or mortar and pestle) and/or dried before being powdered/crushed. Other methods known in the art for grinding may be used. The plant material may then be subjected to a solvent extraction process.

The solvents that can be used for the extraction procedures include water (e.g., distilled and demineralised), hydroalcohol (e.g. water and alcohol mixture containing more than or about 10%, 20%, 30%, 40%, 50%, 60%, 70%, 80%, 90% alcohol), organic solvent, alcohol, or any mixture of at least two of these solvents. Hydroalcoholic and alcoholic extracts may be an ethanolic or methanolic extract, propanolic, butanolic, glycerol, or an extract obtained from a CMO aliphatic alcohol. In another embodiment, the extracts are obtained using an organic solvent, examples of which include ketones (such as CMO ketones), hydrocarbons (such as hexane), organic acids, esters (such as ethyl acetate), ethers (such as ethyl ether), alkyl chlorides (such as methylene chloride), etc. A mixture of any two or more (e.g., 3 solvents, 4 solvents, etc.) of the foregoing solvents may be used with or without water (e.g., methanol and ethanol). The solvent is evaporated to generate an extract/residue. The extract can be in a liquid (reconstituted) or dried form.

Figure 2:
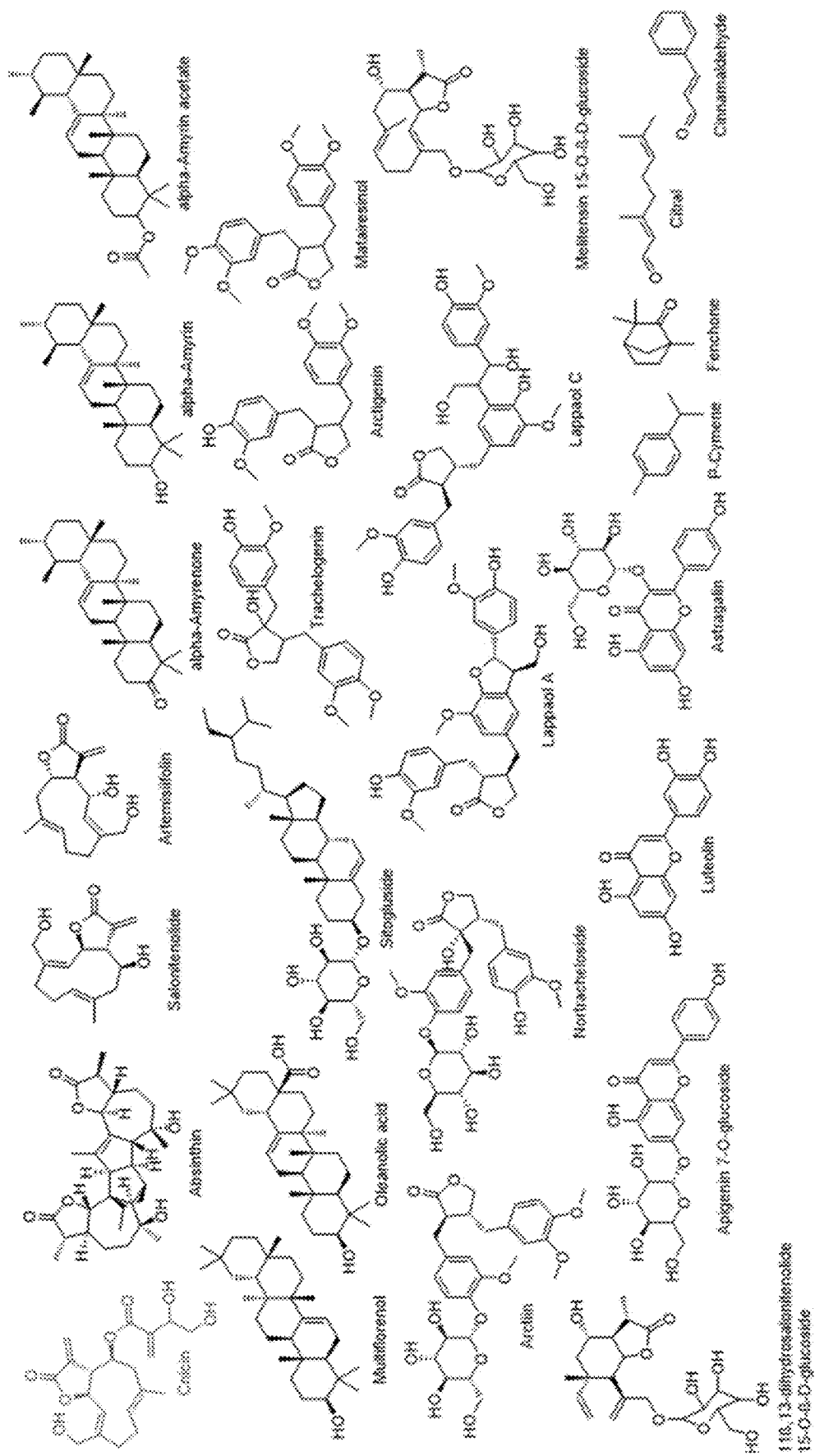
FIG. 2. The chemical constituents in CBE.

In some embodiments, compounds within the extract are isolated or independently synthesized for administration to a subject. FIG. 2 provides the compounds within *C. benedictus* extract. In some embodiments, an isolated or purified cnicin is provided. Cnicin is a sesquiterpene lactone, esterified with a substituted acrylic acid, and belonging to the germacranolide class of natural products. It is mainly found in *Cnicus benedictus*, and is also present in spotted knapweed plants, where highest and lowest concentrations are found in the leaves (0.86-3.86% cnicin) and stems respectively.

The term "isolated" or "purified" refers to a preparation of a compound that is isolated from, or otherwise substantially free of, other compounds, e.g. those compounds normally found in a plant extract. A "purified" compound refers to a compound having a purity of at least 90%, e.g. a purity of at least 95%, 96%, 97%, 98%, or 99%.

Compositions containing cnicin, e.g. a plant extract or an isolated/purified cnicin, may be used to treat a coronavirus infection. The term "treat/treating" refers to eliciting the desired biological response, i.e., a therapeutic effect which comprises one or more of a decrease/reduction in infection or infection symptom, a decrease/reduction in the severity of the infection (e.g., reduction or inhibition of viral adsorption, reduction or inhibition of viral replication, etc.), and an increased survival time of the affected host animal, following administration of the agent/composition.

Coronaviruses are a group of related RNA viruses that cause diseases in mammals and birds. In humans and birds, they cause respiratory tract infections that can range from mild to lethal. Mild illnesses in humans include some cases of the common cold (which is also caused by other viruses, predominantly rhinoviruses), while more lethal varieties can cause SARS, MERS, and COVID-19. Coronaviruses constitute the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases. Exemplary coronaviruses that may be treated with the compositions of the disclosure include, but are not limited to, SARS-Cov, SARS-Cov-2, MERS-Cov, HCoV-0C43, HCoV-HKU1, HCoV-229E, and HCoV-NL63.

Without being so limited, the medicaments/pharmaceutical compositions of the disclosure may be administered orally, for example in the form of tablets, coated tablets, dragees, hard or soft gelatin capsules, solutions, emulsions or suspensions. Administration can also be carried out rectally, for example using suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as ophthalmological preparations or an aerosol, for example in the form of a spray, such as a nasal spray.

The active agent (e.g. the extract or cnicin) may be combined with pharmaceutically acceptable excipients/carriers. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

The compositions can also be administered in combination therapy, e.g., combined with at least one other agent able to treat or inhibit coronavirus infection.

In some embodiments, the active agent (e.g. cnicin) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Figure 1:
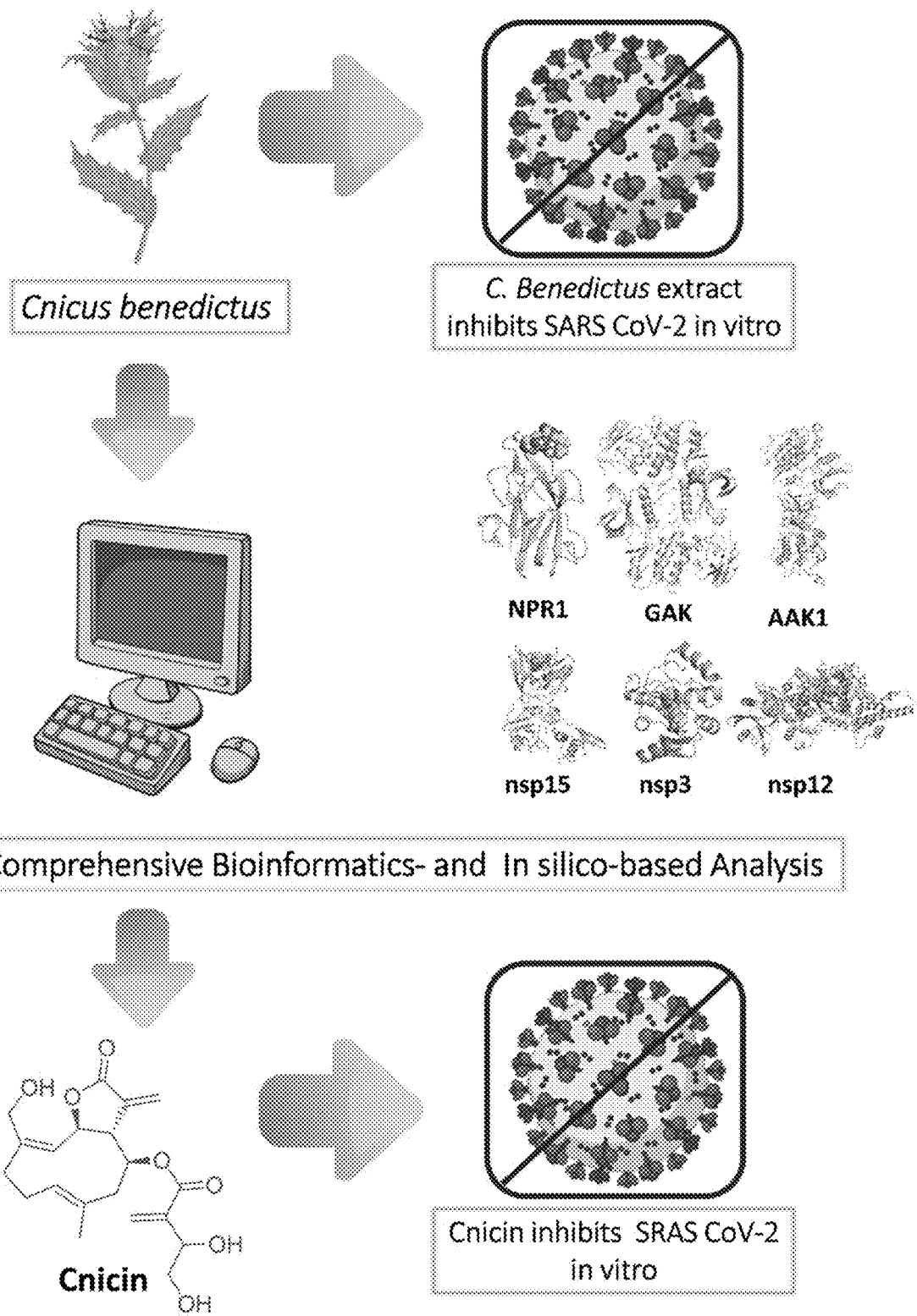
FIG. 1. Diagram of the workflow of the study.

SARS-CoV-2 is a significant global threat. Despite the presence of different COVID-19 vaccines, the discovery of proper antiviral therapeutics is an urgent necessity. Nature is considered as a historical trove for drug discovery, especially in global crises. Screening of a natural products and plant crude extracts library led to the identification of *C. benedictus* extract (CBE) as a promising candidate. To find out the main chemical constituents responsible for the extract antiviral activity, we utilized the recently reported SARS CoV-2 structural information in comprehensive in silico investigations (e.g. ensemble docking and physics-based molecular modeling). As a result, we constructed a protein-protein and protein-compound interaction network suggesting cnicin as the most promising anti-SARS CoV-2 hit that might inhibit multiple viral targets. The subsequent in vitro validation confirmed cnicin to impede the viral replication of SARS CoV-2 in a dose-dependent manner with an $IC_{50}$ value of 1.18 μg/mL. FIG. 1 summarizes the strategy applied in the current study.

Materials and Methods

Preparation of CBE

*C. benedictus* aerial parts were obtained in January 2019 from Faculty of Pharmacy, Minia University, East Desert, Minia, Egypt, and authenticated by Prof. AbdelHalim Mohamed, Horticulture Research Institute, Agriculture Research Center, Giza, Egypt. All collected plant material (1 kg) were washed thoroughly, dried, and extracted with 80% ethanol (3×500 mL). Subsequently, the resulted liquid extract was dried using rotary evaporator (IKA™, Germany) to obtain the dried extract, which was kept at 4° C.

Preparation of *C. benedictus*'s Pure Compounds

Apigenin 7-O-glucoside, astragalin, arctiin, nortracheloside, luteolin, sitogluside, and cnicin were isolated from the CBE according to the previous protocols[14,15,16,17,18]. All of the aforementioned compounds were also purchased (Sigma Aldrich, Santacruz Biotech, USA and BioCrick, Sichuan Province, P. R. China) to ensure the antiviral's maximum possible purity for in vitro testing.

Data Preparation

Chemical constituents of *C. benedictus* (FIG. 2) were identified depending on an extensive literature search using Web of Knowledge, Reaxys, and Dictionary of Natural Products. The exact isomeric structures of these retrieved molecules were obtained from the PubChem database[19].

Regarding the SARS-CoV-2 proteins, all currently available viral and non-viral proteins relevant to the COVID-19 were retrieved from the Swiss-Model repository (swissmodel.expasy.org/repository/species/2697049) and String database (string-db.org/cgi/covid.pl)[20,21].

Ensemble Docking

We used AutoDock Vina software in all docking experiments[22]. All the prepared *C. benedictus* compounds were docked against all of the collected proteins. The binding site of each protein was determined according to its co-crystallized ligand. Homology models along with other proteins without co-crystallized ligands were subjected to a blind docking protocol in which the software predicted all possible binding sites. To account for protein flexibility, we used the MDS-derived conformers sampled every 10 ns for docking experiments (i.e. ensemble docking)[23]. Subsequently, we ranked top hits according to their calculated binding energies. Docking poses were analyzed and visualized by Pymol software[22].

Molecular Dynamic Simulation

MD simulations were performed by Desmond v. 2.2[24,25], the MDS machine of Maestro software[26] using the OPLS-AA 2005 force field. Proteins systems were built via System Builder option, where it was embedded in an orthorhombic box of TIP3P waters together with 0.15 M $Na^+$ and ions with 20 A° solvent buffer. For permeability studies, lipid bilayer systems were built according to the previous report of Lomize and Pogozheva 2019[27]. Afterwards, the prepared systems were energy minimized and equilibrated for 20 ns. All compounds' parameters and topologies were calculated using both the online software Ligand Reader & Modeler (charmm-gui.org/?doc=input/ligandrm)[28] and the VMD Force Field Toolkit (ffTK)[29]. Binding free energy calculations (ΔG) were accomplished using the free energy perturbation (FEP) method via the online software Absolute Ligand Binder[28] and the MDS software NAMD 2.6[30]. Simulations were run at 310 K in the NPT ensemble with the Nose-Hoover thermostat and Martyna-Tobias-Klein barostat using an anisotropic coupling. We used the best binding pose for each compound inside the corresponding protein binding site to investigate their binding stability and mode of interactions. Finally, generated trajectories were visualized and analyzed by VMD software[29].

Networks Construction

We constructed three networks (FIG. 3): (i) protein-protein interaction (PPI) network that showed the actual binding and interactions between viral-viral and viral-host proteins depending on the data obtained from the Swiss-Model repository; (ii) protein-pathway network to indicate the role of each group of proteins in the viral pathogenesis; (iii) compound-protein interaction (CPI) network depending on the docking and MDS results. We constructed a connection between C. benedictus compounds and both viral and host target proteins if the compound got a docking score <−6 kcal/mol, and remained stable inside the corresponding protein binding site across 100 ns of MDS. All of the above networks were constructed and summarized in a single figure (FIG. 3) using Cytoscape 3.8.2 software (cytoscape.org/)[31].

In silica Permeability Studies

Along with the MDS study, we further utilized a neural-network-based software study the cellular permeability of the top-hits compounds. The PerMM web server (per-mm.phar.umich edu/)[32] is a computational tool for assessing the molecules' passive permeability across lipid bilayers. The applied protocol was dependent on inhomogeneous solubility-diffusion theory using the DOPC bilayer model. PerMM calculates the following parameters: (i) energy profiles along the lipid bilayer, (ii) membranes binding affinity, and molecules' permeability coefficients. The software's database currently contains ~500 molecules, (e.g. small synthetic organic compounds and natural products). The ADME properties and their drug-likeness of the top-hits were also calculated using the online website "swissadme.ch/"[33].

In Vitro Antiviral Assay

Virus and Cells

DMEM (Dulbecco's Modified Eagle's medium) supplemented with 2% Penicillin/Streptomycin and 10% FBS was used to maintain Vero-E6 cells at 37° C. and 5% $CO_2$. The cells were infected with hCoV-19/Egypt/NRC-3/2020 isolate at a multiplicity of infection (MOI) of 0.1 in an infection medium (DMEM) supplemented with 1% L-1-tosylamido-2-phenylethyl chloromethyl ketone (TPCK)-treated trypsin, 4% FBS, and 1% Penicillin/Streptomycin. Fresh infection medium was used after two hours to replace the infection medium containing virus inoculum and incubated for three days. Cell supernatant was centrifuged at 2500 rpm for 5 min for purification, and the supernatant was then titrated using plaque assay.

MTT Cytotoxicity Assay

The $IC_{50}$ (half-maximal inhibitory concentration) was determined by preparing stock solutions of the extracts and test compounds in 10% DMSO and further diluted with DMEM. Vero-E6 cells with the previously reported (MTT) method[34] were used to test the cytotoxic activity of the test compounds and extracts. In brief, the cells were plated in 96-well plates and incubated for 24 h at 37° C. in 5% $CO_2$ (100 μL/well at a density of $3 \times 10^5$ cells/mL). The cells were then treated with different concentrations of extracts/the tested compounds in triplicates. The supernatant was discarded after another 24 h, and cell monolayers were washed three times with sterile 1× PBS. MTT solution was added to each well and then incubated at 37° C. for 4 h. The produced formazan crystals were dissolved with 200 μL of acidified isopropanol (0.04 M HCl in absolute isopropanol=0.073 mL HCL in 50 mL isopropanol). Thereafter, the absorbance of formazan solutions was measured at $\lambda_{max}$ 540 nm using a multi-well plate reader. The following equation was applied to calculate the percentage of cytotoxicity compared to the untreated cells:

$$\% \text{ cytotoxicity} = \frac{(\text{absorbance of cells without treatment} - \text{absorbance of cells with treatment}) \times 100}{\text{absorbance of cells without treatment}}$$

The produced plot of % cytotoxicity versus sample concentrations was then used to calculate the $IC_{50}$s.

Viral Inhibitory Concentration 50 ($IC_{50}$) Determination $2.4 \times 10^4$ Vero-E6 cells were placed in 96 well plate, and then incubated overnight in a humidified 37° C. incubator under 5% $CO_2$ condition. The cell monolayers were then washed once with PBS and subjected to virus adsorption for 1 h at room temperature. Afterwards, the cells were further overlaid with 50 μL of DMEM mixed with the test compounds and the extracts. The cells were incubated for 72 h, fixed with 4% paraformaldehyde for 20 min and then stained for 15 min with 0.1% crystal violet. Subsequently, 100 μL methanol was used to dissolve the crystal violet and the optical density was measured using Anthos Zenyth 200rt plate reader (Anthos Labtec Instruments, Heerhugowaard, Netherlands) at 570 nm. The $IC_{50}$ of the compound is the concentration that reduces the virus-induced cytopathic effect (CPE) by 50%, relative to the virus control.

Quantitative Real Time Measurement of SARS-CoV-2 mRNA Expression

The RNA extraction of expressed SARS-CoV-2 mRNA in infected treated and untreated cell monolayers was performed using QIAamp Viral RNA Mini Kit according to manufacturer instructions. To assess the viral mRNA expression in infected/treated and infected/untreated Vero E6 cells, TaqMan Real-time RT-PCR assay was performed. Briefly, 100 ng of extracted RNA were mixed with TaqMan primers to quantify SARS-CoV-2 mRNA (targeting orf1a: HKU-ORF1b-nsp14F: 5'-TGGGGYTTTACRGGTAACCT-3' (SEQ ID NO: 1), HKU-ORF1b-nsp141P Taqman Probe: 5'-FAM-TAGTTGTGATGCWATCATGACTAG-TAMRA-3' (SEQ ID NO: 2), HKU-ORF1b-nsp14R: 5'-AACRCGCT-TAACAAAGCACTC-3' (SEQ ID NO: 3) together with the other components of Verso 1-step RT-qPCR Kit plus Rox (Invitrogen) in recommended volumes (up to 50 μl reaction) and thermal protocol conditions.

Results 3.1. Compound-Protein and Protein-Protein Interactions Networks

Among the tested plant extracts in our extracts library, CBE showed the most viral inhibitory activity in vitro. Consequently, to determine the probable active compounds in CBE, we subjected all major compounds in this extract to a comprehensive in silico screening. First, we reviewed all of the compounds previously reported from C. benedictus (FIG. 2). Twenty-five compounds belonging to different chemical classes were retrieved in this step. Subsequently, all of these 25 compounds were subjected to an inverse ensemble docking protocol against all the reported SARS CoV-2 proteins to find out the probable molecular targets for each compound. Top hits (got docking score <−6 kcal/mol) were further subjected to 10-20 ns of MDS to refine the docking experiments. Finally, we selected only compounds that were stable inside the protein binding sites during the simulations. As a result, we suggested cnicin, apigenin 7-O-glucoside, astragalin, arctiin, and nortracheloside to be the main anti-SARS CoV 2 metabolites in CBE (FIG. 2, 3).

Figure 3:
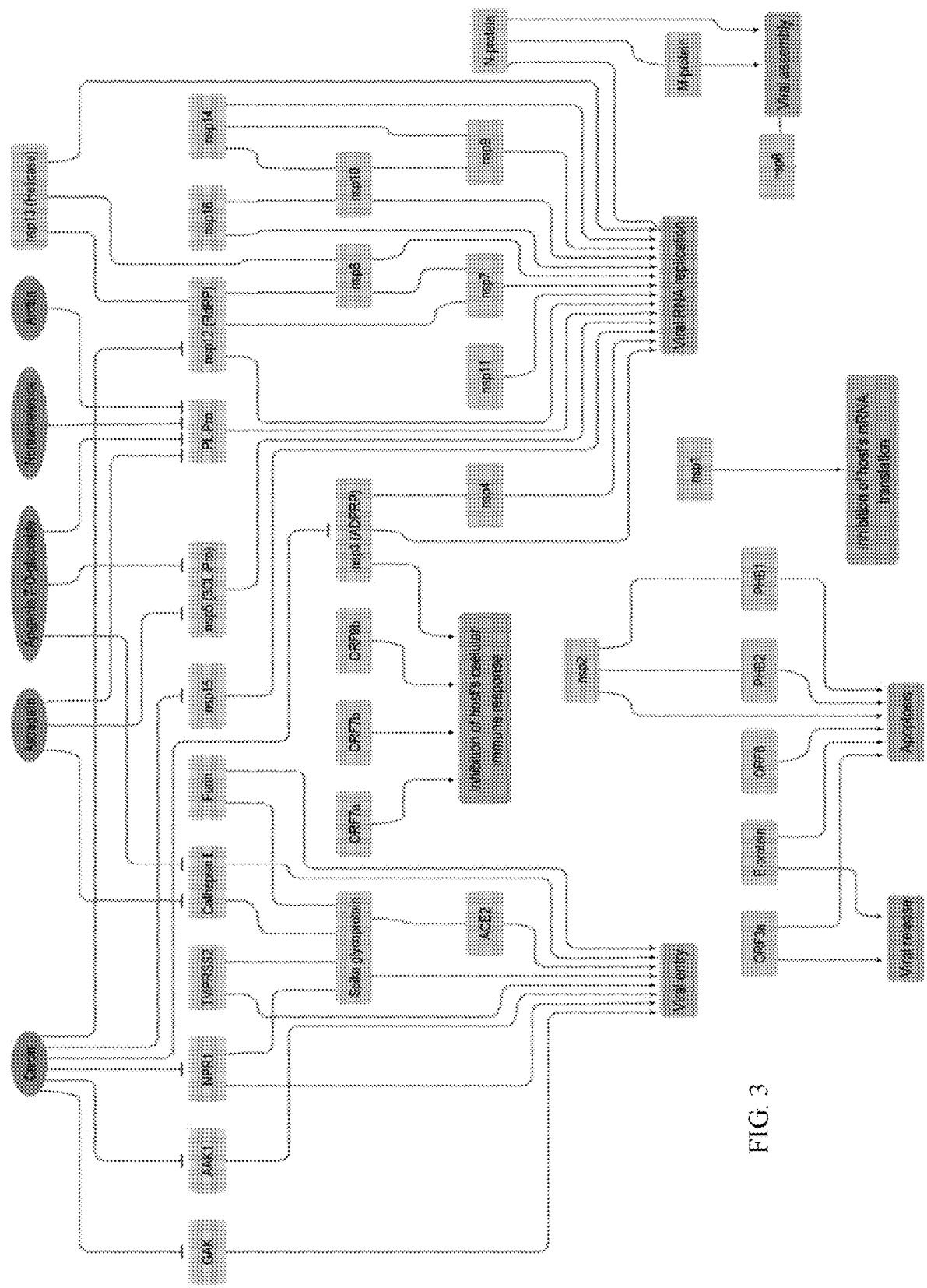
FIG. 3. PPI network of the viral and host proteins indicating the involved pathway along with the CPI network which shows the top-scoring compound in CBE.
Figure 4:
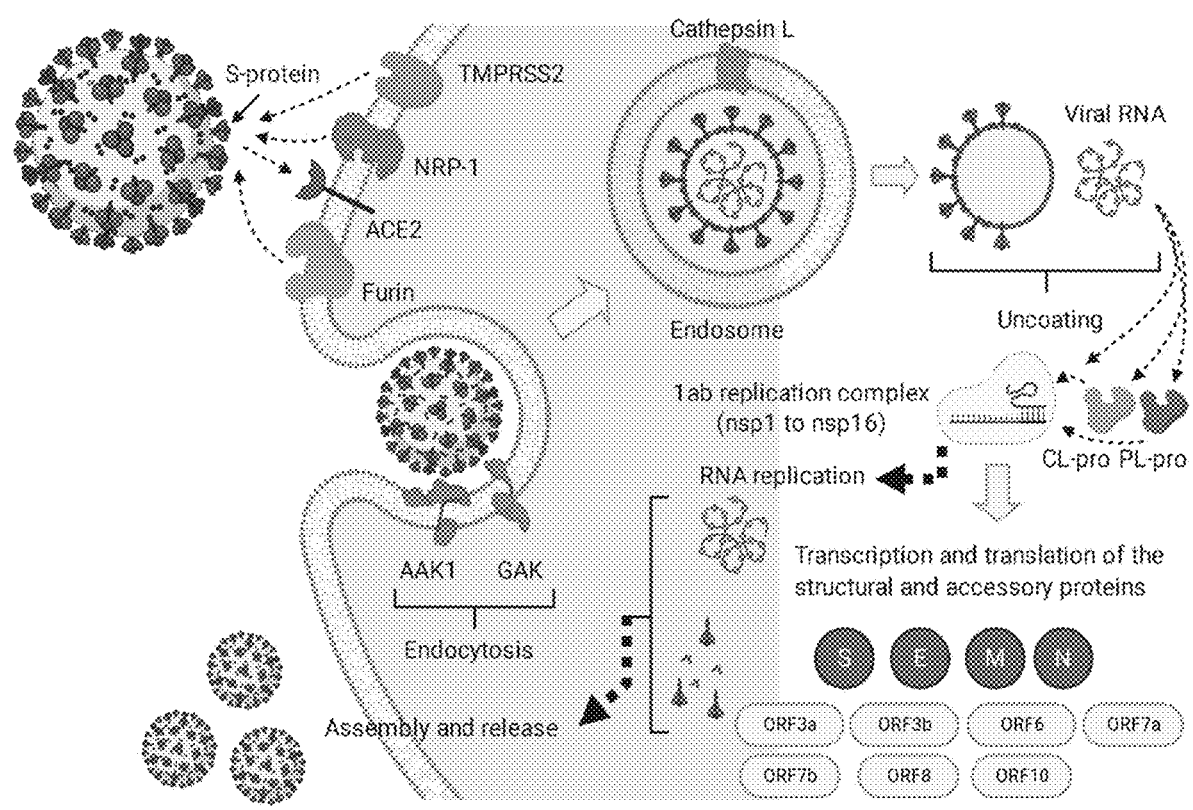
FIG. 4. Pathway diagram indicates the pathogenesis of SARS-CoV-2 inside the host cell. This pathway was constructed based on the data retrieved from KEGG website (genome.jp/kegg-bin/show_pathway?hsa05171+H02398).

On the other hand, we also reviewed all the viral protein interactions with each other or human proteins to construct a completed protein-protein interactions (PPI) map for the virus inside the human host cell. We utilized a number of bioinformatics platforms (e.g. SWISS-MODEL; swissmodel.expasy.org/repository/species/2697049, and KEGG; genome.jp/kegg-bin/show_pathway?map05171+H02398 #) together with the recent literature to construct this PPI map (FIG. 3, 4). All the reported PPI in this map are actual interactions extracted from co-crystallized complexes.

RNA dependent RNA polymerase (nsp12), nsp10, helicase (nsp13), nsp9, as well as nsp 14 are the most interacting nonstructural proteins (nsp) in the replication complex (1ab) which control the viral replication. However, the spike glycoprotein (S-protein) was the most interacting and vital protein involved in the viral entry.

As shown in FIG. 3, apigenin 7-O-glucoside, astragalin, arctiin, and nortracheloside were predicted to interact and inhibit CL-pro and PL-pro. These two enzymes have an essential role in viral RNA replication as they activate the replication complex (1ab) so that the latter can initiate the viral RNA replication[35]. On the other side, cnicin was found to putatively interact and inhibit six proteins that are involved in viral RNA replication, entry, and the inhibition of the host immune response (FIG. 3, 4). The key protein RdRP was among the cnicin targets indicating a direct inhibition of RNA replication. Cnicin also targeted ADP ribose phosphatase (ADPRP, nsp3) which has a dual action in viral RNA replication and inhibition of the host innate immunity[36]. Regarding the viral entry, cnicin was also found to inhibit neuropilin 1 (NPR-1) that activates the viral S-protein to be ready for the subsequent endocytosis[37]. Besides, it targeted both AAK1 and GAk that have a crucial role in the viral endocytosis process[38].

Our in silico findings highlighted that apigenin 7-O-glucoside, astragalin, arctiin, nortracheloside and particularly cnicin were the most probable active components in CBE and can fight the virus inside the host cell via multiple mechanisms.

Validation of the In Silico Analysis

Figure 5A:
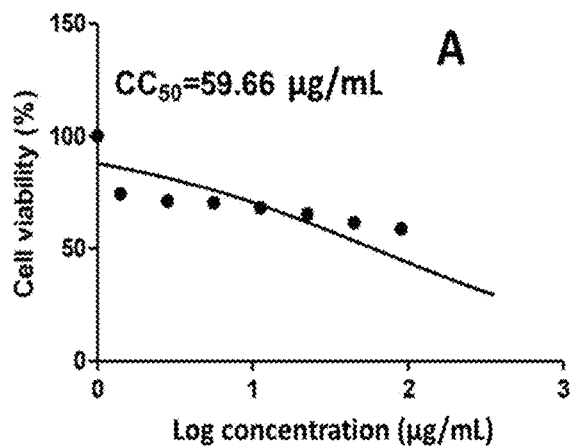
FIGS. 5A-C. Cytotoxicity (A), in vitro anti-SARS-CoV-2 activity (B) of cnicin, and the viral mRNA % inhibition (C). Nonlinear regression analysis in GraphPad Prism® software (version 5.01) was used to calculate the $IC_{50}$ values.
Figure 5B:
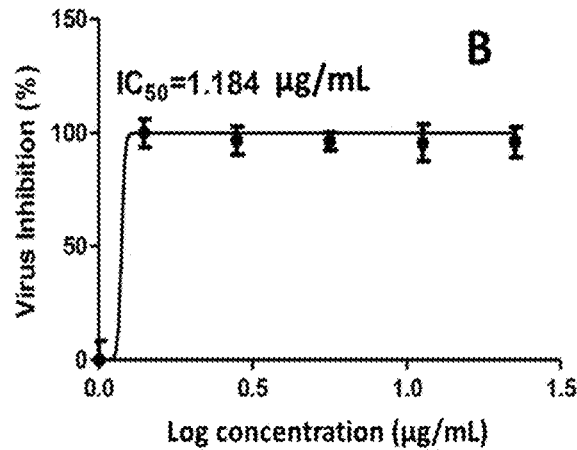
Figure 5C:
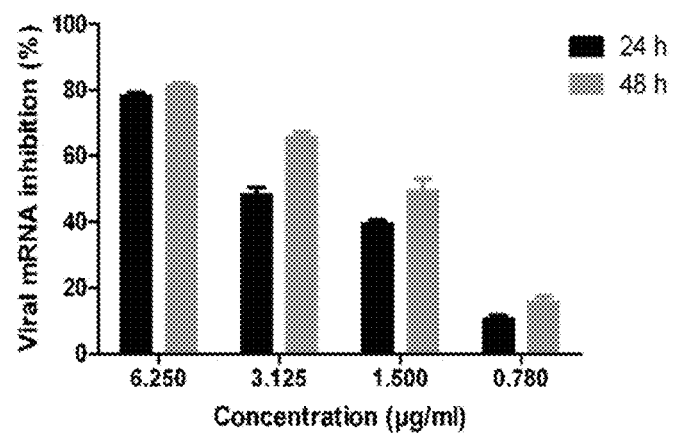

To validate our in silico-derived hits, we evaluated their antiviral activity against the clinical SARS-CoV-2 viral isolate in Vero E6 cells. Firstly, the five selected compounds (cnicin, apigenin 7-O-glucoside, astragalin, nortracheloside and arctiin) were evaluated for their cytotoxicity against Vero E6 cells. All of them showed $IC_{50}$ over 50 μg/mL. Afterwards, the SARS CoV-2 infected Vero E6 cells were incubated with each of the tested compounds at different concentrations. The antiviral activity was then evaluated by determining the viral copy numbers in the cell supernatant via qRT-PCR. Among the predicted compounds, only cnicin exhibited antiviral effect against SARS CoV-2 and showed dose-dependent inhibition of the viral replication with $IC_{50}$ of 1.18 μg/mL (FIG. 5). Furthermore, the inhibitory effect of cnicin on the viral mRNA was measured and normalized to infected untreated cells. Interestingly, cnicin resulted in significant viral mRNA inhibition at different concentrations at 24 h and 48 h post treatment (FIG. 5C). The poor antiviral activity of other metabolites (>100 μg/mL) might be attributed to their high polarity that could hinder the permeability across the cell membrane[39]. Accordingly, these finding suggests that the antiviral activity of CBE ($IC_{50}$=10.1 μg/mL) is likely due to its cnicin content. To further validate our in silico protocol, we tested two of the lowest scoring compounds (luteolin and sitogluside) against SARS CoV-2, and as predicted, both compounds were inactive (100 μg/mL).

Molecular Interactions Study

Although apigenin 7-O-glucoside, astragalin, arctiin, and nortracheloside showed molecular interactions with three targets (FIG. 3), they were inactive against in vitro SARS-CoV-2 testing. Such outcomes could be attributed to their low permeability across the cell membrane which is related to their topological polar surface area (tPSA) and permeability coefficients[27]. Molecules that can easily cross the cell membrane through passive diffusion usually have tPSA less than 140 Å$^2$. Additionally, they should have permeability coefficients >-4[27,32]. Apigenin 7-O-glucoside, astragalin, arctiin, and nortracheloside were found to have high tPSA ranging from 160.3 to 190.4 Å$^2$. Moreover, when subjected to MDS-based calculation of their permeability coefficients[27,32], all of them showed very low permeability coefficients ranging from -14.17 to -10.8, and remained stagnant outside the lipid bilayer, where they attached to the polar part. Such polar glycosylated metabolites are well-known for their poor permeability[39] across cellular membranes. Hence, their therapeutic potential is greatly affected by this pharmacokinetic factor.

On the other hand, cnicin, which has a tPSA of 113.3 Å$^2$, was able to cross the lipid bilayer much more freely with a permeability coefficient of -3.52. Furthermore, other calculated physicochemical parameters were acceptable, according to Lipinski' s and Veber' s rules of drug-likeness[40, 41].

Regarding its binding modes inside the active sites of the predicted targets, cnicin got the highest binding free energy ($\Delta G$=-12.2 kcal/mol) against RdRP (nsp12) at the binding site of N-terminal nidovirus RdRp-linked nucleotidyltransferase (NiRAN) domain[42]. It achieved high binding stability during a 100 ns MDS (RMSD ~2.01 Å) through 5 strong H-bonds in addition to 3 other hydrophobic interactions (FIG. 6) with multiple amino acid residues involved in the interaction with the co-crystallized ligand adenine diphosphate (ADP). This binding pocket of the NiRAN domain was recently reported as a promising target for antiviral therapy development[42].

Similarly, cnicin achieved interesting binding free energy with ADPRP ($\Delta G$=-11.8 kcal/mol). Also, it adopted a binding mode (FIG. 6) inside the active site compared to the co-crystallized ligand ADP ribose, where all the molecule's oxygen atoms were involved in H-bonding leading to high stability during the MDS (RMSD ~2.08). Recently, ADPRP was found to have a crucial role in viral replication and interference with the host immune response[36].

Figure 6E:
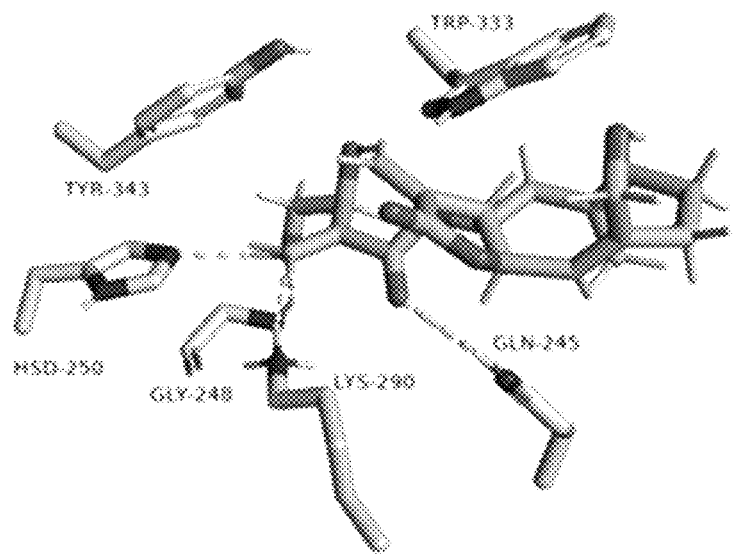
Figure 6F:
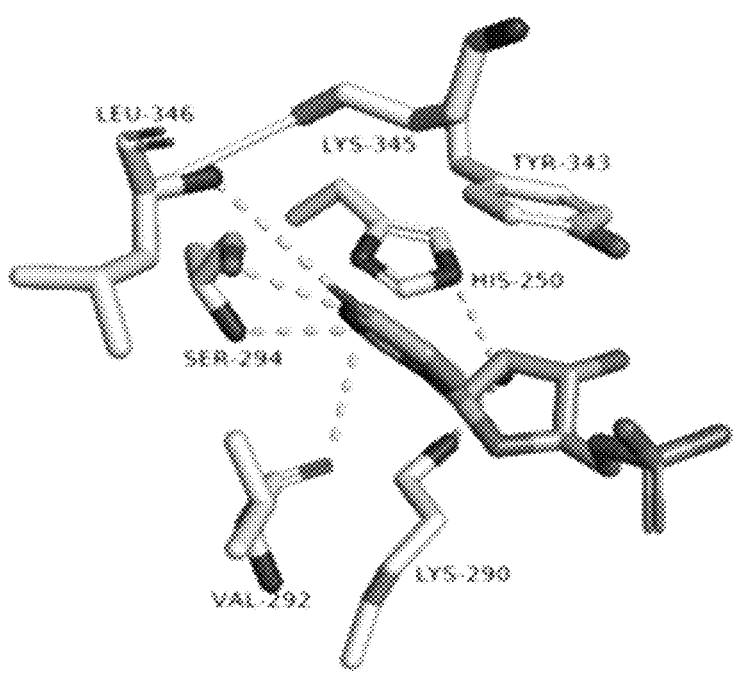
Figure 7A:
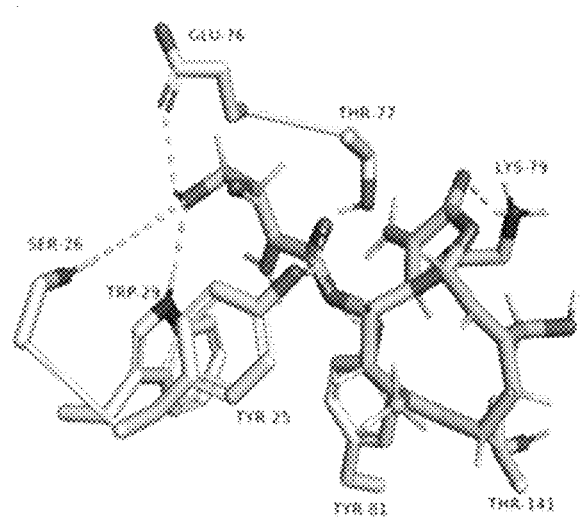
FIGS. 7A-F. Binding modes of cnicin inside the binding sites of three human targets involved in the viral entry; NRP-1, AAK1, and GAK (A, C, and E, respectively) during 100 ns MDS along with the binding modes of the corresponding co-crystallized ligands (B, D, and F, respectively).
Figure 7B:
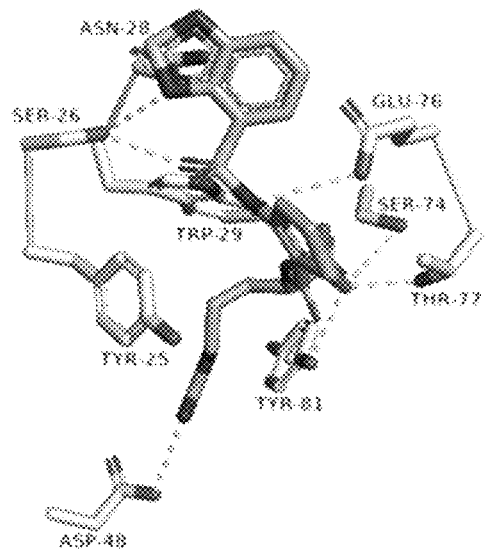
Figure 7C:
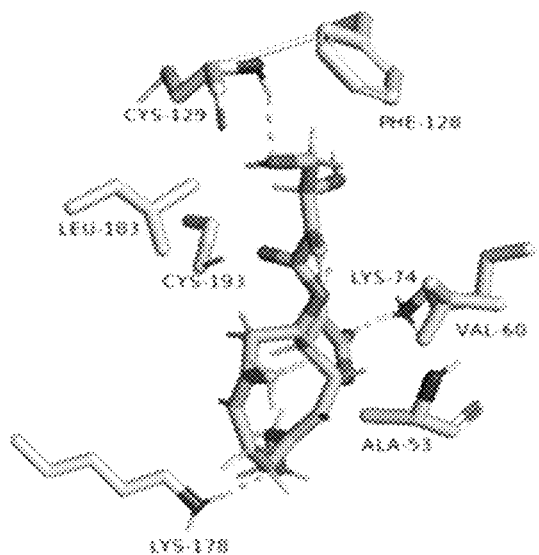
Figure 7D:
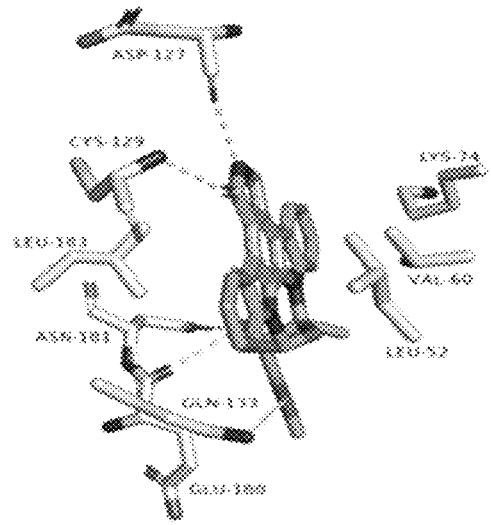
Figure 7E:
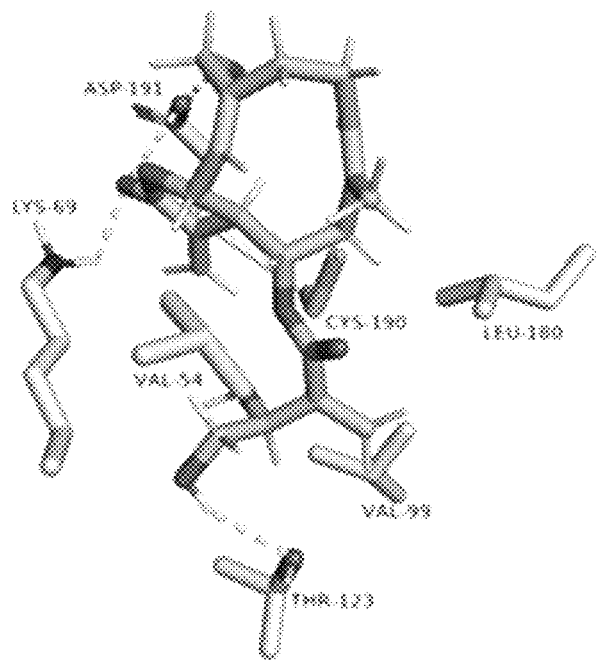
Figure 7F:
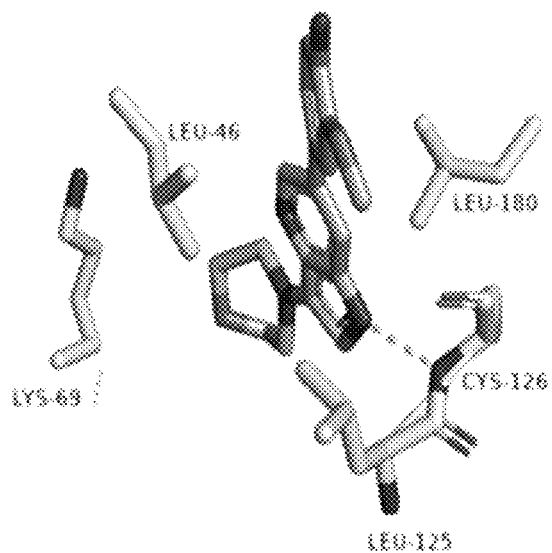

Cnicin was also able to achieve a perfect binding affinity toward the viral endoribonuclease (nsp15) with a binding free energy lower than that of the co-crystallized ligand ($\Delta G$=-10.6 and -9.5 kcal/mol, respectively). Moreover, it was more stable inside the binding site than the co-crystallized ligand during the MDS (RMSD ~2.2 Å) and such stability was achieved through three strong H-bonds (<2 Å) and two hydrophobic interactions (FIG. 6). This enzyme proved to have a crucial role in viral replication, and hence, is considered an anti-SARS-CoV-2 target[43].

Regarding the human proteins involved in the viral entry inside the cell, cnicin was able to target three of them. The first one is neuropilin-1 (NRP-1), where it got the highest binding free energy that was even better than the co-crystallized ligand ($\Delta G$=-13.9 and -9.1 kcal/mol, respectively). During MDS, cnicin was highly stabilized (RMSD ~1.44 A) inside the binding pocket (B1 domain) through a network of strong H-bonds (<2.5 Å) in addition to multiple hydrophobic interactions with the molecule's hydrocarbon body (FIG. 6). NRP-1 is a surface glycoprotein that regulates a number of fundamental processes in carcinogenesis.

This protein was recently also involved in SARS-COV-2 uptake by epithelial/endothelial cells following S-protein cleavage by furin[44,45].

Furthermore, cnicin was able to bind to both Adaptor-Associated Kinase 1 (AAK1) and Cyclin G-Associated Kinase (GAK). These two serine-threonine protein kinases are essential for the SARS-CoV-2 endocytosis. Besides, they regulate the intracellular viral operation throughout the assemblage and release of several non-related RNA viruses; for example, hepatitis C, rabies, and Ebola virus[38]. Cnicin achieved significant binding stability inside the active site of both kinases through the course of MDS (RMSD ~1.8, 1.2 Å; −10.2, −9.3 kcal/mol, respectively), and binding modes convergent to the co-crystallized inhibitors (FIG. 7).

Taken together, the in vitro testing results together with the virtual and physics-based modelling experiments demonstrate that cnicin is a SARS-CoV-2 multi-target inhibitor that can be used as an antiviral therapeutic agent.

Discussion

SARS-CoV-2 still threatens global health, particularly in developing countries. Moreover, it keeps evolving into new strains with new clinical features[46]. Despite different developed COVID-19 vaccines, the search for new therapeutics is an urgent necessity.

Natural products were the main pipeline of human medicine throughout history, and they are still able to provide effective therapeutics for our current health crisis. Our continuous screening of small natural products and crude extracts library for potential anti-SARS CoV-2 therapeutics led to the discovery of CBE as a promising candidate.

C. benedictus (aka Blessed thistle) has traditionally been used as a bitter to enhance appetite and digestion. It has also exhibited antimicrobial and anti-inflammatory activities in previous in vitro and in vivo studies[14]. Cnicin is one of the major chemical constituents of Blessed thistle, and was proven to exhibit a broad antimicrobial activity (e.g. antiparasitic toward Schistosoma mansoni, antibacterial)[47,48]. C. benedictus is generally considered safe, and in the USA, it is used as a component in Benedictine Liqueur™[14].

With the aid of a number of bioinformatics tools (e.g. COVID-19 protein databases, network pharmacology, molecular docking, and molecular dynamic simulations), we constructed a complete interactions network of the viral proteins with each other and with human-based proteins involved in its cellular entry. Besides, we suggested a number of C. benedictus metabolites to be the active antiviral agents inside its crude extract (CBE) depending on our employed in protocol: (i) extensive ensemble docking of all C. benedictus previously reported metabolites against all SARS CoV-2, proteins; (ii) physics-based simulations of all the best hits to refine the first docking step further. Four glycosylated compounds and cnicin were found to interact with nine targets involved in the viral replication, entry, and the host cellular immune response, During in vitro testing, cnicin inhibited SARS CoV-2 viral replication in a dose-dependent way with an $IC_{50}$ of 1.18 µg/mL, respectively, while the glycosylated compounds were not. In addition, it showed considerable safety profile (Si=CC50/IC50=70.3) for further development as an antiviral therapeutic agent.

Further dynamic simulations were conducted to study the molecular interactions of these compounds. Low cellular permeability of the glycosylated constituents has appeared the main cause of lacking in vitro activity.

The active compound, cnicin, possesses excellent drug-like properties and high cellular permeability. Additionally, it achieved stable bindings with six protein targets in modes comparable with the previously reported inhibitors suggesting cnicin as a drug candidate for CoVs.

Ivermectin was the first reported natural product-derived compound that showed promising in vitro inhibitory activity against SARS CoV-2[49]. Later, it showed promising clinical outcomes[50,13]. Similar to our findings with cnicin in this study, ivermectin exerts its antiviral effect via targeting multiple targets, particularly host-based ones[51].

Conclusion

Our virtual and physics-based modelling experiments together with the in vitro testing results shed light toward cnicin as a coronavirus multi-target inhibitor.

REFERENCES

1. Kumar, D., Chauhan, G., Kalra, S., Kumar, B., Gill, M. S., 2020. A perspective on potential target proteins of COVID-19: Comparison with SARS-CoV for designing new small molecules. Bioorganic chemistry, 104326.
2. Cascella, M., Rajnik, M., Cuomo, A., Dulebohn, S. C., Di Napoli, R. 2020. Features, evaluation and treatment coronavirus (COVID-19), In: Statpearls [internet]. StatPearls Publishing.
3. Singh, P., Mishra, N., Singh, N., Nisha, R., Pal, R. R., Singh, S., Maurya, P., Saraf, S. A., 2020. Credible Protein Targets and Curative Strategies for COVID-19: a Review. SN Comprehensive Clinical Medicine, 1-10.
4. Pillaiyar, T., Meenakshisundaram, S., Manickam, M., 2020. Recent discovery and development of inhibitors targeting coronaviruses. Drug Discovery Today 25, 668-688.
5. Zheng, K.-H.C., Yuen, K.-Y., Lau, C. C., Tsang, A. K., Lau, J. H., Bai, R., 2012. Patrick C Y Woo, Susanna K P Lau, Carol S F Lam. J. Virol 86, 3995.
6. Wang, C., Horby, P. W., Hayden, F. G., Gao, G. F., 2020a. A novel coronavirus outbreak of global health concern. The Lancet 395, 470-473.
7. Wang, J., 2020. Fast identification of possible drug treatment of coronavirus disease-19 (COVID-19) through computational drug repurposing study. Journal of Chemical Information and Modeling.
8. Yang, Y., Islam, M. S., Wang, J., Li, Y., Chen, X., 2020. Traditional Chinese medicine in the treatment of patients infected with 2019-new coronavirus (SARS-CoV-2): a review and perspective. International journal of biological sciences 16, 1708.
9. Wondmkun, Y. T., Mohammed, O. A., 2020. A Review on Novel Drug Targets and Future Directions for COVID-19 Treatment. Biologics: Targets & Therapy 14, 77.
10. Abd El-Mordy, F. M., El-Hamouly, M. M., Ibrahim, M. T., Abd El-Rheem, G., Aly, O. M., Abd El-kader, A. M., Youssif, K. A., Abdelmohsen, U. R., 2020. Inhibition of SARS-CoV-2 main protease by phenolic compounds from Manilkara hexandra (Roxb.) Dubard assisted by metabolite profiling and in silico virtual screening. RSC Advances 10, 32148-32155.
11. Owis, A. I., El-Hawary, M. S., El Amir, D., Aly, O. M., Abdelmohsen, U. R., Kamel, M. S., 2020. Molecular docking reveals the potential of Salvadora persica flavonoids to inhibit COVID-19 virus main protease. RSC Advances 10, 19570-19575.
12. Sayed, A. M., Khattab, A. R., AboulMagd, A. M., Hassan, H. M., Rateb, M. E., Zaid, H., Abdelmohsen, U. R., 2020. Nature as a treasure trove of potential anti-SARS-CoV drug leads: a structural/mechanistic rationale. RSC Advances 10, 19790-19802.

13. Hashim, H. A., Maulood, M. F., Rasheed, A. M., Fatak, D. F., Kabah, K. K., & Abdulamir, A. S. (2020). Controlled randomized clinical trial on using Ivermectin with Doxycycline for treating COVID-19 patients in Baghdad, Iraq. medRxiv.
14. Ulbricht, C., Basch, E., Dacey, C., Dith, S., Hammerness, P., Hashmi, S., . . . & Weissner, W. (2008). An evidence-based systematic review of blessed thistle (Cnicus benedictus) by the Natural Standard Research Collaboration. Journal of dietary supplements, 5(4), 422.
15. Al-Snafi, A. E. (2016). The constituents and pharmacology of Cnicus benedictus-A review. The Pharmaceutical and Chemical Journal, 3(2), 129-135.
16. Ulubelen, A., & Berkan, T. (1977). Triterpenic and steroidal compounds of Cnicus benedictus. Planta Medica, 31(04), 375-377.
17. Sólyomváry, A., Tóth, G., Kraszni, M., Noszál, B., Molnár-Perl, I., & Boldizsár, I. (2014). Identification and quantification of lignans and sesquilignans in the fruits of Cnicus benedictus L.: Quantitative chromatographic and spectroscopic approaches. Microchemical Journal, 114, 238-246.
18. Peng, Y., Jian, Y., Zulfiqar, A., Li, B., Zhang, K., Long, F., . . . & Wang, W. (2017). Two new sesquiterpene lactone glycosides from Cnicus benedictus. Natural Product Research, 31(19), 2211-2217.
19. Kim, S., Thiessen, P. A., Bolton, E. E., Chen, J., Fu, G., Gindulyte, A., . . . & Wang, J. (2016). PubChem substance and compound databases. Nucleic acids research, 44(D1), D1202-D1213.
20. Elbe, S., & Buckland-Merrett, G. (2017). Data, disease and diplomacy: GISAID's innovative contribution to global health. Global Challenges, 1(1), 33-46.
21. Gordon, D. E., Jang, G. M., Bouhaddou, M., Xu, J., Obernier, K., White, K. M., . . . & Tummino, T. A. (2020). A SARS-CoV-2 protein interaction map reveals targets for drug repurposing. Nature, 1-13.
22. Seeliger, D., & de Groot, B. L. (2010). Ligand docking and binding site analysis with PyMOL and Autodock/Vina. Journal of computer-aided molecular design, 24(5), 417-422.
23. Sayed, A. M., Alhadrami, H. A., El-Gendy, A. O., Shamikh, Y. I., Belbahri, L., Hassan, H. M., . . . & Rateb, M. E. (2020). Microbial natural products as potential inhibitors of SARS-CoV-2 main protease (Mpro). Microorganisms, 8(7), 970.
24. Bowers, K. J., Chow, D. E., Xu, H., Dror, R. O., Eastwood, M. P., Gregersen, B. A., Salmon, J. K. (2006, November). Scalable algorithms for molecular dynamics simulations on commodity clusters. In SC'06: Proceedings of the 2006 ACM/IEEE Conference on Supercomputing (pp. 43-43). IEEE.
25. Release, S. (2017). 3: Desmond molecular dynamics system, DE Shaw research, New York, N.Y., 2017. Maestro-Desmond Interoperability Tools, Schrödinger, New York, N.Y.
26. Schrodinger L L C (2009) Maestro, Version 9.0. New York, N.Y., USA.
27. Lomize, A. L., & Pogozheva, I. D. (2019). Physics-Based Method for Modeling Passive Membrane Permeability and Translocation Pathways of Bioactive Molecules. Journal of chemical information and modeling, 59(7), 3198-3213.
28. Jo, S., Kim, T., Iyer, V. G., & Im, W. (2008). CHARMM-GUI: a web-based graphical user interface for CHARMM. Journal of computational chemistry, 29(11), 1859-1865.
29. Humphrey, W., Dalke, A., & Schulten, K. (1996). VMD: visual molecular dynamics. Journal of molecular graphics, 14(1), 33-38.
30. Phillips, J. C., Braun, R., Wang, W., Gumbart, J., Tajkhorshid, E., Villa, E., . . . & Schulten, K. (2005). Scalable molecular dynamics with NAMD. Journal of computational chemistry, 26(16), 1781-1802.
31. Kohl, M., Wiese, S., & Warscheid, B. (2011). Cytoscape: software for visualization and analysis of biological networks. In Data mining in proteomics (pp. 291-303). Humana Press.
32. Lomize, A. L., Hage, J. M., Schnitzer, K., Golobokov, K., LaFaive, M. B., Forsyth, A. C., & Pogozheva, I. D. (2019). PerMM: A Web Tool and Database for Analysis of Passive Membrane Permeability and Translocation Pathways of Bioactive Molecules. Journal of chemical information and modeling, 59(7), 3094-3099.
33. Daina, A., Michielin, O., & Zoete, V. (2017). SwissADME: a free web tool to evaluate pharmacokinetics, drug-likeness and medicinal chemistry friendliness of small molecules. Scientific reports, 7, 42717.
34. Mosmann, T. (1983). Rapid colorimetric assay for cellular growth and survival: application to proliferation and cytotoxicity assays. Journal of immunological methods, 65(1-2), 55-63.
35. Su, H. X., Yao, S., Zhao, W. F., Li, M. J., Liu, J., Shang, W. J., . . . & Yu, K. Q. (2020). Anti-SARS-CoV-2 activities in vitro of Shuanghuanglian preparations and bioactive ingredients. Acta Pharmacologica Sinica, 41(9), 1167-1177.
36. Michalska, K., Kim, Y., Jedrzejczak, R., Maltseva, N. I., Stols, L., Endres, M., & Joachimiak, A. (2020). Crystal structures of SARS-CoV-2 ADP-ribose phosphatase (ADRP): from the apo form to ligand complexes. bioRxiv.
37. Vitiello, A., La Porta, R., & Ferrara, F. (2020). Sacubitril, valsartan and SARS-CoV-2. BMJ Evidence-Based Medicine.
38. Gil, C., Ginex, T., Maestro, I., Nozal, V., Barrado-Gil, L., Cuesta-Geijo, M. A., . . . & Martinez, A. (2020). COVID-19: Drug targets and potential treatments. Journal of Medicinal Chemistry.
39. Fang, Y., Cao, W., Xia, M., Pan, S., & Xu, X. (2017). Study of structure and permeability relationship of flavonoids in Caco-2 cells. Nutrients, 9(12), 1301.
40. Lipinski, C. A., Lombardo, F., Dominy, B. W., & Feeney, P. J. (1997). Experimental and computational approaches to estimate solubility and permeability in drug discovery and development settings. Advanced drug delivery reviews, 23(1-3), 3-25.
41. Veber, D. F., Johnson, S. R., Cheng, H. Y., Smith, B. R., Ward, K. W., & Kopple, K. D. (2002). Molecular properties that influence the oral bioavailability of drug candidates. Journal of medicinal chemistry, 45(12), 2615-2623.
42. Chen, J., Malone, B., Llewellyn, E., Grasso, M., Shelton, P. M., Olinares, P. D. B., . . . & Kapoor, T. M. (2020). Structural basis for helicase-polymerase coupling in the SARS-CoV-2 replication-transcription complex. Cell, 182(6), 1560-1573.
43. Kim, Y., Wower, J., Maltseva, N., Chang, C., Jedrzejczak, R., Wilamowski, M., . . . & Joachimiak, A.

(2020). Tipiracil binds to uridine site and inhibits Nsp15 endoribonuclease NendoU from SARS-CoV-2. bioRxiv.
44. Jarvis, A., Allerston, C. K., Jia, H., Herzog, B., Garza-Garcia, A., Winfield, N., . . . & Hartzoulakis, B. (2010). Small molecule inhibitors of the neuropilin-1 vascular endothelial growth factor A (VEGF-A) interaction. Journal of medicinal chemistry, 53(5), 2215-2226.
45. Cantuti-Castelvetri, L., Ojha, R., Pedro, L. D., Djannatian, M., Franz, J., Kuivanen, S., . . . & Smura, T. (2020). Neuropilin-1 facilitates SARS-CoV-2 cell entry and infectivity. Science, 370(6518), 856-860.
46. Wise, J. (2020). Covid-19: New coronavirus variant is identified in UK.
47. Queiroz, L. S., Ferreira, E. A., Mengarda, A. C., Almeida, A. D. C., Pinto, P. D. F., Coimbra, E. S., . . . & Da Silva Filho, A. A. (2020). In vitro and in vivo evaluation of cnicin from blessed thistle (Centaurea benedicta) and its inclusion complexes with cyclodextrins against Schistosoma mansoni. Parasitology Research, 1-13.
48. Steinbach, A., Scheidig, A. J., & Klein, C. D. (2008). The unusual binding mode of cnicin to the antibacterial target enzyme MurA revealed by X-ray crystallography. Journal of medicinal chemistry, 51(16), 5143-5147.
49. Caly, L., Druce, J. D., Catton, M. G., Jans, D. A., & Wagstaff, K. M. (2020). The FDA-approved drug ivermectin inhibits the replication of SARS-CoV-2 in vitro. Antiviral research, 104787.
50. Rajter, J. C., Sherman, M. S., Fatteh, N., Vogel, F., Sacks, J., & Rajter, J. J. (2020). Use of Ivermectin Is Associated With Lower Mortality in Hospitalized Patients With Coronavirus Disease 2019: The ICON Study. Chest.
51. Jans, D. A., & Wagstaff, K. M. (2020). Ivermectin as a Broad-Spectrum Host-Directed Antiviral: The Real Deal?. Cells, 9(9), 2100.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of inhibiting coronavirus replication in cells in vitro, comprising
   selecting cells infected with a coronavirus, and
   contacting the cells with a composition comprising cnicin, wherein the composition comprises purified cnicin at a purity of at least 99%.

2. The method of claim 1, wherein the coronavirus is SARS-CoV-2.

3. The method of claim 1, wherein the coronavirus is MERS-CoV.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
tggggyttta crggtaacct                                              20

<210> SEQ ID NO 2
<211> LENGTH: 24
<212> TYPE: DNA
<213> ORGANISM: Artificial Sequence
<220> FEATURE:
<223> OTHER INFORMATION: synthetic primer

<400> SEQUENCE: 2
tagttgtgat gcwatcatga ctag                                         24

<210> SEQ ID NO 3
<211> LENGTH: 21
<212> TYPE: DNA
<213> ORGANISM: Artificial Sequence
<220> FEATURE:
<223> OTHER INFORMATION: synthetic primer

<400> SEQUENCE: 3
aacrcgctta acaaagcact c                                            21